US008557607B2

(12) United States Patent
Penades et al.

(10) Patent No.: US 8,557,607 B2
(45) Date of Patent: Oct. 15, 2013

(54) MAGNETIC NANOPARTICLES

(75) Inventors: Soledad Penades, Seville (ES); Manuel Martin-Lomas, Seville (ES); Jesus Martines De La Fuente, Seville (ES); Thomas William Rademacher, Oxford (GB)

(73) Assignees: Consejo Superior de Investigacione Cientificas, Madrid (ES); Midatech Limited, London (GB)

( * ) Notice: Subject to any disclaimer, the term of this patent is extended or adjusted under 35 U.S.C. 154(b) by 1242 days.

(21) Appl. No.: 10/559,957

(22) PCT Filed: Jun. 7, 2004

(86) PCT No.: PCT/GB2004/002408
§ 371 (c)(1),
(2), (4) Date: Apr. 19, 2006

(87) PCT Pub. No.: WO2004/108165
PCT Pub. Date: Dec. 16, 2004

(65) Prior Publication Data
US 2006/0233712 A1  Oct. 19, 2006

(30) Foreign Application Priority Data
Jun. 9, 2003 (GB) .................... 0313259.4

(51) Int. Cl.
*G01N 33/553* (2006.01)
*A61K 49/00* (2006.01)
(52) U.S. Cl.
USPC .................. 436/526; 436/518; 424/9.322

(58) Field of Classification Search
USPC .................. 436/526, 518; 424/9.322
See application file for complete search history.

(56) References Cited

U.S. PATENT DOCUMENTS

| 4,452,773 | A | | 6/1984 | Molday | |
| 5,260,050 | A | * | 11/1993 | Ranney | 424/9.351 |
| 6,207,134 | B1 | * | 3/2001 | Fahlvik et al. | 424/9.322 |
| 6,270,748 | B1 | * | 8/2001 | Annan et al. | 424/9.322 |
| 6,531,304 | B1 | | 3/2003 | Bonnemann et al. | |
| 6,955,639 | B2 | * | 10/2005 | Hainfeld et al. | 600/1 |
| 2002/0068187 | A1 | | 6/2002 | O'Connor et al. | |

FOREIGN PATENT DOCUMENTS

| EP | 0 428 412 | 5/1991 |
| WO | 9724224 | 7/1997 |
| WO | WO 99/61911 | 12/1999 |
| WO | WO9961911 | * 12/1999 |

(Continued)

OTHER PUBLICATIONS

Fleming, D.A., et al., "Chemically Functional Alkanethiol Derivitized Magnetic Nanoparticles," Mat. Res. Soc. Symp. Proc., 746:207-212, (2003).

(Continued)

*Primary Examiner* — Mark Shibuya
*Assistant Examiner* — Pensee Do
(74) *Attorney, Agent, or Firm* — Patrick J. Hagan; Dann, Dorfman, Herrell and Skillman, P.C.

(57) ABSTRACT

Materials and methods for making small magnetic particles, e.g. clusters of metal atoms, which can be employed as a substrate for immobilizing a plurality of ligands. Also disclosed are uses of these magnetic nanoparticles as therapeutic and diagnostic reagents, and in the study of ligand-mediated interactions.

3 Claims, 8 Drawing Sheets

(56) References Cited

FOREIGN PATENT DOCUMENTS

| WO | WO 02/32404 | 4/2002 |
|---|---|---|
| WO | WO 02/093140 | 11/2002 |
| WO | WO 03/086660 | 10/2003 |
| WO | WO 2004/033488 | 4/2004 |

OTHER PUBLICATIONS

Teranishi, T., et al., "Fabrication of gold nanoparticle superlattices and their optical and electronic properties," Gold, pp. 978-982, (2003). (5 pages).

Srikanth, H., et al., "Dynamic transverse susceptibility in Au-Fe-Au nanoparticles," Materials Science and Engineering, A304-306, 901-904, (2001).

Park, S-J., et al., "Synthesis and Magnetic Studies of Uniform Iron Nanorods and Nanospheres," J. Am. Chem. Soc., 122:8581-8582, (2000).

Niemeyer, C.M., "Nanoparticles, proteins, and nucleic acids: biotechnology meets materials science," Angew. Chem. Int. Ed., 40:4128-4158, (2001).

Bergemann, C., et al., "Magnetic ion-exchange nano- and microparticles for medical, biochemical and . . . ," Journal of Magnetism and Magnetic Materials, 194:45-52, (1999).

Whitesides, G.M., et al., "Magnetic separations in biotechnology," Trends in Biotechnology, 1:144-148, (1983).

Sun, S., et al., "Monodisperse FePt Nanoparticles and Ferromagnetic FePt Nanocrystal Superlattices," Science, 287:1989-1992, (2000).

Shafi, K.V.P.M., et al., "Surfactant-assisted self-organization of cobalt nanoparticles in a magnetic fluid," Advanced Materials, 10:590-593, (1998). (4 pages).

Fried, T., et al., "Ordered two-dimensional arrays of ferrite nanoparticles," Advanced Materials, 13:1158-1161, (2001). (4 pages).

Moumen, N., et al., "Controlled preparation of nanosize cobalt ferrite magnetic particles," Journal of Magnetism and Magnetic Materials, 149:67-71, (1995).

Suslick, K.S., et al., "Sonochemical Synthesis of Iron Colloids," J. Am. Chem. Soc., 118:11960-11961, (1996).

Sun, S., et al., "Size-controlled synthesis of magnetite nanoparticles," J. Am. Chem. Soc., 124:8204-8205, (2002).

Guo, Q., et al., "Patterned Langmuir-Blodgett films of monodisperse nanoparticles of iron oxide using soft lithography," J. Am. Chem. Soc., 125:630-631, (2003).

Sun, S., et al., "Polymer mediated self-assembly of magnetic nanoparticles," J. Am. Chem. Soc., 124:2884-2885, (2002).

Josephson, L., et al., "High-efficiency intracellular magnetic labeling with novel superparamagnetic-tat peptide conjugates," Bioconjugate Chem., 10:186-191, (1999).

Lewin, M., et al., "Tat peptide-derivatized magnetic nanoparticles allow in vivo tracking and recovery of progenitor cells," Nature Biotechnology, 18:410-414, (2000).

Josephson, L., et al., "Magnetic nanosensors for the detection of oligonucleotide sequences," Angew. Chem. Int. Ed., 40:3204-3206, (2001).

de la Fuente, J., et al., "Gold glyconanoparticles as water-soluable polyvalent models to study carbohydrate interactions," Angew. Chem. Int. Ed., 40:2257-2261, (2001).

Barrientos, A.G., et al., "Gold glyconanoparticles: synthetic polyvalent ligands mimicking glycocalyx-like surfaces as tools for . . . ," Chem. Eur. J., 9:1909-1921, (2003).

Zhou, W.L., et al., "Nanostructures of gold coated iron core-shell nanoparticles and the nanobands assembled under magnetic field," Eur. Phys. J. D, 16:289-292, (2001).

Mykhaylyk, O., et al., "Glial brain tumor targeting of magnetite nanoparticles in rats," J. Magnetism and Magnetic Materials, 225:241-247, (2001).

Jordan, A., et al., "Magnetic fluid hyperthermia (MFH): cancer treatment with AC magnetic field induced . . . ," J. Magnetism and Magnetic Materials, 201:413-419, (1999).

Josephson, L., et al., "Near-infrared fluorescent nanoparticles as combined MR/optical imaging probes," Bioconjugate Chem., 13:554-560, (2002).

Taton, T.A., et al., "Scanometric DNA array detection with nanoparticle probes," Science, 289:1757-1760, (2000).

Gambardella, P., et al., "Giant Magnetic Anisotropy of Single Cobalt Atoms and Nanoparticles," Science, 300:1130-1133, (2003).

Di Felice, R., et al., "DFT study of cysteine adsorption on Au(111)," J. Phys. Chem. B, 107:1151-1156, (2003).

Davidovic, D., et al., "Spectroscopy, Interactions, and Level Splittings in Au Nanoparticles," Physical Review Letters, 83:1644-1647, (1999).

Vitos, L., et al., "Size-dependent paramagnetic-ferromagnetic phase transition in palladium clusters," Physical Review B, 62:R11957-R11960, (2000).

Hernaiz, M., et al., "A model system mimicking glycospingolipid clusters to quanitfy carbohydrate self-interactions . . . ," Angew. Chem. Int. Ed. 41:1554-1557, (2002).

Billas, I.M., et al., "Magnetism from the atom to the bulk in iron, cobalt, and nickel clusters," Science, 265:1682-1684, (1994).

J. Rojo et al., "Gold Glyconanoparticles as New Tools in Antiadhesive Therapy", ChemBioChem, 5: 291-297 (2004).

R.T. Gordon et al., "Intracellular Hyperthermia—A Biophysical Approach to Cancer Treatment Via Intracellular Temperature and Biophysical Alterations", Medical Hypotheses, 5: 83-102 (1979).

* cited by examiner

MAGNETIC NANOPARTICLES

FIELD OF THE INVENTION

The present invention relates to magnetic nanoparticles, and in particular to magnetic nanoparticles having immobilised ligands and their use in studying the interaction of these ligands with other species. The present invention further relates to applications of the nanoparticles, for example for screening, diagnosis and therapy.

BACKGROUND OF THE INVENTION

The development of methodologies to produce nanoparticles with bio-responsive properties has opened the way for producing useful tools for molecular diagnostics, therapeutics and biotechnology [1]. Metal, semiconductor and magnetic colloidal nanoparticles are presently under intensive study for potential applications [2].

Nanoparticles containing paramagnetic materials such as iron oxide have been made which exhibit unusually strong magnetic properties under external magnetic fields. These magnetic nanoparticles can be used in many biomedical applications, including cell separation, in vivo cell and tissue labelling, contrast enhancement in magnetic resonance imaging, tumour targeting, hyperthermia therapies and drug delivery.

For such applications, the nanoparticles should preferably be small enough to avoid provoking an immune response and to be taken up by cells, where necessary. It is also useful if the size of the particles can be controlled as the particles should be of approximately the same size so they display the same magnetic properties. The particles should also preferably be chemically stable, so they are not broken down by the body.

In is also preferred that magnetic nanoparticles for use in biomedicine are soluble, especially in water, in order that they may be stored and administered effectively. Ideally, such particles would be stable in solution and would not aggregate, either when stored before use or in the body. Magnetic nanoparticles tend to clump together in solution because they attract each other. If this happened in the body it could impede blood flow and potentially be dangerous; in colloidal solution it would make the colloid difficult to use.

Previously, commercially available iron oxide particles have been used in cell sorting and separation [3]. Monodisperse magnetic nanoparticles of Fe/Pt [4], Co and Co/Fe [5], Fe [6], and iron oxides [7] have recently been synthesised by solution chemistry for materials applications.[8]. Iron oxide nanoparticles coated with cross-linked dextran to prevent clumping have also been described, see for example WO 03/005029.

Ideally, the magnetic nanoparticles are made of elemental magnetic metal rather than metal oxide, as elemental metal is a better enhancer of magnetic imaging. However, such nanoparticles are often chemically unstable, as the metal may oxidise. One possibility for increasing the chemical stability of magnetic nanoparticles is to synthesise them from a magnetic metal with a passive metal to stabilise the magnetic metal.

US 2002/0068187 discloses surfactant protected gold-iron core-shell nanoparticles synthesised by means of reverse micelles. However, this method is complex, requiring three synthesis steps. The multi-layered composition of the resulting particles also increases the lower size limit for the particles, which can be a disadvantage if very small particles are required [14].

U.S. Pat. No. 6,254,662 discloses use of FePt and CoPt alloy nanoparticles to form nanocrystalline thin films on a solid surface, for use in making ultra-high density recording media. Other uses of the films are mentioned in the parent, including use as magnetic bias films and magnetic tips for magnetic force microscopy, but biomedical applications are not envisaged.

For many of the applications described above, it is necessary to link the nanoparticles to biologically active molecules such as ligands that bind to intracellular or extracellular molecules. Such ligands may for example be carbohydrate, nucleic acid or protein.

U.S. Pat. No. 6,514,481 discloses iron oxide nanoparticles coated with a silica shell, where the shell is linked to a targeting molecule such as a peptide via a spacer molecule. WO 02/098364 and WO 01/19405 disclose magnetic metal oxide nanoparticles coated with dextran and functionalised with peptides and oligonucleotides. Similar strategies have been used to prepare nanoparticles for intracellular labelling [9] and as nanosensors.[10]. All these methods are time-consuming multi-step methods requiring that the nanoparticles be coated with dextran or silica, the coated nanoparticles be functionalised so they will bind the ligand, and finally that the ligand be bound to the nanoparticles.

WO 03/073444 discloses superparamagnetic nanoparticles having a cores formed from Au and Fe metal atoms in a ratio of at least 3:7. The application says that ligands can be linked to the core via a sulphide group and that the nanoparticles are used for forming nanoelectronic devices. The cores of the nanoparticles have diameters in the range of 5 nm to 50 nm.

WO 02/093140 discloses magnetic nanowires which comprise one or more segments and functional groups or ligands associated with a at least one of said segments. The nanowires have a diameter in the range of about 10-300 nm and a length from 10 nm to tens of microns. The segments of the nanowires may be formed from materials such as gold, silver, platinum, copper, iron and cobalt in pure or alloyed form and the functional groups may be atoms or groups of atoms that are capable of further chemical reactivity such as reacting with a ligand to attach the ligand to the wire, or to bind a target molecule. Although a range of possible ways of associating the ligands and the nanowires are proposed, the examples rely on the ionic interaction between ligands containing carboxylic acid groups and the nanowire.

U.S. Pat. No. 6,531,304 discloses a nanoscale colloid formed from metal alloys which is reacted and non-covalently binds a polysaccharide or sugar "modifier".

WO 02/32404 discloses water soluble nano-tools for studying carbohydrate mediated interactions [11], [12]. These tools are gold glyconanoparticles and cadmium sulphide glyco-nanodots incorporating carbohydrate antigens. These water soluble gold and semiconductor nanodots are stable for months in physiological solutions and present exceptionally small core sizes. They are resistant to glycosidases and do not present cytotoxicity. They are also useful platforms for basic studies of carbohydrate interactions [13] and are tools for biotechnological and biomedical applications. However, these nanoparticles are not magnetic.

There is therefore a continuing need in the art for stable magnetic nanoparticles which are bound to ligands to make them suitable for biomedical uses, which can be synthesised to a desired size, and which can be produced by a simple, reliable synthesis method.

SUMMARY OF THE INVENTION

Broadly, the present invention provides materials and methods for producing magnetic nanoparticles that are particularly suitable for use in biomedical applications. In particular, the present invention provides magnetic nanoparticles which are employed as a substrate for immobilising a plurality of ligands, where the ligands are covalently linked to the core of the nanoparticle. The ligands may comprise carbohydrate groups, peptides, protein domains, nucleic acid segments or fluorescent groups. These nanoparticles can then be used to study ligand mediated interactions, e.g. with other carbohydrates, proteins or nucleic acids, and as therapeutics and diagnostic reagents. In some embodiments, the particles have the further advantage that they are soluble, e.g. in water and a range of organic solvents, and can be used in a variety of homogeneous application formats.

The inventors have now developed magnetic nanoparticles with size in the nanometer scale which form stable colloidal aqueous solutions (ferrofluids). The methods described herein constitute a simple and versatile approach by which neoglycoconjugates of significant carbohydrates are covalently linked to gold/iron clusters as a method for tailoring stable, water-soluble, magnetic glyconanoparticles with globular shapes and highly polyvalent carbohydrate surfaces. The methodology also allows the attachment of many other molecules directly to the nanocluster.

Accordingly, in a first aspect, the present invention provides a particle comprising a magnetic core, such as a metallic core, linked to a plurality of ligands. The ligands may comprise carbohydrate groups, peptides, protein domains, nucleic acid segments or other biological macromolecules. The ligands may additionally or alternatively comprise fluorescent groups.

Preferably, where the magnetic core comprises passive metal atoms and magnetic metal atoms, and the ratio of passive metal atoms to magnetic metal atoms in the core is between about 5:0.1 and about 2:5. More preferably, the ratio is between about 5:0.1 and about 5:1.

As used herein, the term "passive metal" refers to metals which do not show magnetic properties and are chemically stable to oxidation.

The passive metals of the invention may be diamagnetic. "Diamagnetic" refers to materials with all paired electrons which thus have no permanent net magnetic moment per atom. "Magnetic" materials have some unpaired electrons and are positively susceptible to external magnetic fields—that is, the external magnetic field induces the electrons to line up with the applied field, so the magnetic moments of the electrons are aligned.

Magnetic materials may be paramagnetic, superparamagnetic or ferromagnetic. Paramagnetic materials are not very susceptible to external magnetic fields and do not retain their magnetic properties when the external magnetic field is removed. Ferromagnetic materials are highly susceptible to external magnetic fields and contain magnetic domains even when no external magnetic field is present, because neighbouring atoms cooperate so their electron spins are parallel. External magnetic fields align the magnetic moments of neighbouring domains, magnifying the magnetic affect. Very small particles of materials that normally have ferromagnetic properties are not ferromagnetic, as the cooperative effect does not occur in particles of 300 nm or less so the material has no permanent magnetism. However, the particles are still very susceptible to external magnetic fields and have strong paramagnetic properties, and are known as superparamagnetic. Preferably, the nanoparticles of the invention are superparamagnetic.

In one embodiment, the nanoparticle consists of a core comprising passive metal atoms and magnetic metal atoms, which core is covalently linked to a plurality of ligands.

Preferably, the ratio of passive metal atoms to magnetic metal atoms in the core is between about 5:0.1 and about 2:5. More preferably, the ratio is between about 5:0.1 and about 5:1.

In a further aspect, the present invention provides compositions comprising populations of one or more of the above defined particles. In some embodiments, the populations of nanoparticles may have different densities of the same or different ligands attached to the core.

In a further aspect, the present invention provides the above defined particles for use in a method of medical treatment.

In a further aspect, the present invention provides the use of the above defined particles for the preparation of a medicament for the treatment of a condition ameliorated by the administration of the ligand. By way of example, this may occur as the ligand blocks a carbohydrate mediated interaction that would otherwise tend to lead to a pathology.

In this embodiment, the present invention has advantages over prior art approaches for treating conditions involving carbohydrate mediated interactions. As described above, typically the interactions are polyvalent whereas the agent used to treat the interactions are often only capable of modulating one or a few of these interactions. This has the result that it is difficult to deliver an agent to the site of the interaction which is capable of reliably modulating the interaction for the desired therapeutic effect. In contrast to this problem, the present invention provides agents having a plurality of ligands for modulating the carbohydrate mediated interactions, potentially overcoming the difficulty in modulating the polyvalent interactions.

In preferred embodiments, the mean diameter of the core, preferably the metallic core, is between 0.5 and 100 nm, more preferably between 1 and 50 nm, more preferably between 1 and 20 nm. More preferably, the mean diameter of the core is below 5 nm, more preferably below 2.5 nm, and still more preferably below 2 nm. The mean diameter can be measured using techniques well known in the art such as transmission electron microscopy.

The core material can be a metal (e.g. Au, or another passive metal atom) or may be formed of more than one type of atom. Preferably, the core material is a composite or an alloy of a passive metal and a magnetic metal. Preferred passive metals are Au, Ag, Pt or Cu and preferred magnetic metals are Fe and Co, with the most preferred composite being Au/Fe. Other composites or alloys may also be used. Nanoparticle cores may also be formed from alloys including Au/Fe, Au/Cu, Au/Gd, Au/Zn, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between 100 and 500 atoms (e.g. gold atoms), more preferably between about 20 and 500 atoms, and still more preferably between about 50 and 500 atoms, to provide core diameters in the nanometer range. A further preferred example of nanoparticles of the present invention have cores formed from Au atoms and Gd, e.g. Gd III, e.g. having a mean diameter less than 10 nm, more preferably less than 5 nm and most preferably about 2.5 nm. Preferred particles of this type comprise between about 1-20% Gd atoms and 99 to 80% Au atoms, and more preferably between about 1-10% Gd and 99 to 90% Au, based on the ratio of the ratio of respective metal atoms present in the core of the nanoparticle.

For some applications, core materials are doped or labelled with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots described elsewhere in this application.

Nanoparticle cores comprising semiconductor atoms can be detected as nanometer scale semiconductor crystals are capable of acting as quantum dots, that is they can absorb light thereby exciting electrons in the materials to higher-energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the nanoparticle of the present invention or ligand(s) may comprise a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET or SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Previously described magnetic nanoparticles for biological applications are almost always made from a magnetic metal oxide, usually iron oxide (magnetite). Nanoparticles comprising Fe and Au have been made, as described above, but have not been used for biological applications or bound to biologically active molecules. These nanoparticles are synthesised as a "nano-onion" comprising a gold core surrounded by an iron shell which is coated with gold to prevent oxidation. The nanoparticles described herein, which have a heterogeneous core comprising both gold and iron atoms, are an improvement over the previously described particles because they can be synthesised in a single simple step, rather than requiring multiple synthesis steps to form the different shells of the nano-onion.

The nanoparticles and the results of their interactions can be detected using a number of techniques well known in the art. These can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance, that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles includes or is doped with atoms which are NMR active then this technique can be used to detect the particles, both in vitro or in vivo, using techniques well known in the art. Nanoparticles can also be detected as described in [18], using a system based on quantitative signal amplification using the nanoparticle-promoted reduction of silver (I) and using a flatbed scanner as a reader. Fluorescence spectroscopy can be used if the nanoparticles include ligands combining carbohydrate groups and fluorescent probes. Also, isotopic labelling of the carbohydrate can be used to facilitate their detection. The ligand linked to the core may comprise one or more carbohydrate (saccharide) groups, e.g. comprising a polysaccharide, an oligosaccharide or a single saccharide group. The ligand may be also be a glycanoconjugate such as a glycolipid or a glycoprotein. In addition to the carbohydrate group, the ligand may additionally comprise one or more of a peptide group, a protein domain, a nucleic acid molecule (e.g. a DNA segment, a single or double stranded nucleic acid molecule, a single or double stranded RNA molecule, a RNA molecule having from 17 to 30 ribonucleotides, e.g. a siRNA or miRNA ligand) and/or a fluorescent probe.

In another embodiment, the ligand may be a peptide or a protein. These may be peptides which binds to receptors on a cell, or they may be antibodies, or therapeutic proteins.

In a further embodiment, the ligand may be a nucleic acid molecule. The nucleic acid may be an oligonucleotide probe that binds to a sequence within the cell. Alternatively, the nucleic acid may comprise an encoding gene sequence for delivery to a cell.

The particles may have more than one species of ligand immobilised thereon, e.g. 2, 3, 4, 5, 10, 20 or 100 different ligands. Alternatively or additionally a plurality of different types of particles can be employed together. Ligands with multiple attachment sites may be linked to a plurality of nanoparticle cores, e.g. 2, 3, or 4 particles. An example of this would be nanoparticle cores linked to the ends of polypeptides or nucleic acid molecules.

In preferred embodiments, the mean number of ligands linked to an individual metallic core of the particle is at least 20 ligands, more preferably at least 50 ligands, and most preferably 60 ligands.

Preferably, the ligands are attached covalently to the core of the particles. Protocols for carrying this out are known in the art, although the work described herein is the first report of the reactions being used to covalently bond ligands to the core of the particle.

This may be carried out by reacting ligands with reductive end groups with gold and iron under reducing conditions. A preferred method of producing the particles employs thiol derivatised carbohydrate moieties to couple the ligands to particles. Thus, in one aspect, the present invention provides a method of preparing the above defined particles, e.g. having a core comprising gold or gold and iron, which core is covalently linked to a plurality of ligands, the method comprising:

(a) synthesizing a sulphide derivative of the ligand; and
  (b) reacting the sulphide derivatised ligand with $HAuCl_4$ (tetrachloroauric acid), and optionally with a ferric salt where iron atoms are present in the core, in the presence of reducing agent to produce the particles. A preferred iron salt is FeCl$_3$.

In some embodiments, the ligand is derivatised with a linker. Preferably, the linker is a disulphide linker, for example a mixed disulphide linker. The linker may further comprise in the chain ethylene groups, peptide or amino acid groups, polynucleotide or nucleotide groups.

An exemplary linker group is represented by the general formula HO—(CH$_2$)$_n$—S—S—(CH$_2$)$_m$—OH, wherein n and m are independently integers between 1 and 5. The ligand can conveniently be linked to the spacer via a suitable group, and in the case of the preferred mixed disulphide linkers via one of the linkers terminal hydroxyl groups. When the nanoparticles are synthesized, the —S—S— of the linker splits to form two thio linkers that can each covalently attach to the core of the nanoparticle via a —S— group. Thus, in a preferred embodiment, the ligand is derivatised as a protected disulphide. Conveniently, the disulphide protected ligand in methanol or water can be added to an aqueous solution of tetrachloroauric acid. A preferred reducing agent is sodium borohydride. Other preferred features of the method are described in the examples below.

The present invention provides a way of presenting a spherical array of ligands having advantages over other types of array proposed in the prior art. In particular, the nanoparticles are soluble in most organic solvents and especially water. This can be used in their purification and importantly means that they can be used in solution for presenting the ligand immobilised on the surface of the particle. The fact that the nanoparticles are soluble has the advantage of presenting the ligands in a natural conformation. For therapeutic applications, the nanoparticles are non-toxic, soluble and stable under physiological conditions.

Magnetic nanoparticles in solution form magnetic colloids known as ferrofluids. Ferrofluids have the fluid properties of a liquid and the magnetic properties of a solid. They have a range of applications, as described below. The main problem encountered with ferrofluids known in the art is their lack of stability: because the magnetic particles attract each other, they will agglomerate after a certain time. Previously used methods of preventing agglomeration include coating the particles with surfactants, crosslinking polymers or polysaccharides. If the nanoparticle is to be bound to a ligand or targeting molecule, a further synthesis step is required.

The particles of the present invention are highly soluble in water and are thus ideal for making ferrofluids. Moreover, the resulting ferrofluids are extremely stable and can be kept for many months without aggregating. Ferrofluids of the invention have been kept for a year with no sign of aggregation. The methods of the present invention allow magnetic nanoparticles that are stable and already bound to functional ligands to be synthesised in a single reaction, rather than requiring the particles first to be coated and then bound to ligands.

Stability may be assessed by eye—a colloidal solution remains transparent in the absence of agglomeration, but becomes opaque once it starts to agglomerate. Alternatively, the presence of flocculation may be determined by transmission electron micrography (TEM), or by comparing the proton NMR spectra of the particles in deuteron water with those of freshly prepared nanoparticles. Preferably, the magnetic particles will show no sign of agglomeration for at least a year after preparation.

In the method described herein, the formation of the core and the covalent linking of the ligand is a simultaneous process, so that the presence of the neoglycoconjugate controls the shape and size of the nanoclusters. The glyconanoparticles prepared in this way have a core of less than 2 nm diameter, which is smaller than any of the magnetic nanoparticles known in the art. Superparamagnetic behaviour is shown at all temperatures and superconducting quantum interference device (SQUID) measurements indicate also the existence of a ferromagnetic component at room temperature. This anomalous magnetic property may be of importance for imaging and cell separations.

The following examples of application for the magnetic nanoparticles and ferrofluids are provided by way of illustration and not limitation to support the wide applicability of the technologies described herein.

In one aspect of the invention, the magnetic properties of the nanoparticles of the invention are exploited in cell separation techniques which eliminate the need for columns or centrifugation. This permits a highly pure population of cells to be obtained quickly and easily. In one embodiment, the nanoparticles may be linked to ligands which specifically bind a receptor on the cell of interest. The nanoparticles may then be added to a cell suspension and the particle-bound cells separated from the rest of the suspension by application of a magnetic field.

This is a highly sensitive as well as efficient method which can be used in many applications, for example in diagnosis of tumours by testing body fluids for the presence of tumour cells. The sensitivity of the technique is a great advantage in this respect.

In a further aspect, the present invention provides a method of determining whether an interaction with a ligand occurs, the method comprising contacting one or more species of ligand-bound nanoparticles with a candidate binding partner and determining whether binding takes place.

In a further aspect, the present invention provides a method of screening for substances capable of binding to a ligand, the method comprising:

contacting nanoparticles as defined herein having a core comprising a passive metal or passive metal and a magnetic metal, which core is covalently linked to a plurality of the ligands, with one or more candidate compounds; and detecting whether the candidate compounds binds to the ligand.

Preferably, the ratio of passive metal atoms to magnetic metal atoms in the core is between about 5:0.1 and about 2:5. More preferably, the ratio is between about 5:0.1 and about 5:1.

In a further aspect, the present invention provides a method of determining the presence in a sample of a substance capable of binding to a ligand, the method comprising contacting the sample with nanoparticles linked to the ligand and determining whether binding takes place. The method may be used to determine the presence or amount of one or more analytes in a sample, e.g. for use in assisting the diagnosis of a disease state associated with the presence of the analyte. The presence of analytes may be signalled by the formation of analyte-nanoparticle aggregates, the presence of which can be detected by measuring the relaxation properties of the fluid in the sample. A change in the relaxation properties indicates the presence of aggregates and hence target molecules.

Where the ligand is a carbohydrate, a range of different carbohydrate mediated interactions are known in the art and could be studied or modulated using the nanoparticles disclosed herein. These include leukocyte-endothelial cell adhesion, carbohydrate-antibody interactions, carbohydrate-protein bacterial and viral infection, immunological recognition of tumour cells, tumour cells-endothelial cells (e.g. to study metastasis) and foreign tissue and cell recognition.

In another aspect, the magnetic nanoparticles and ferrofluids of the invention can be used to treat cancer. Magnetic nanoparticles may be used for hyperthermic treatment of tumours, in which magnetic nanoparticles are injected into tumours and subjected to a high frequency AC or DC magnetic field. Alternatively, near IR light may be used. The heat thus generated by the relaxation magnetic energy of the magnetic material kills the tumour tissue around the particles. In one embodiment of the present invention, tumour cells may be specifically targeted by incorporating tumour-specific antigens into the nanoparticles. This allows tumours not easily reached by injection to be targeted by the therapeutic particles, and avoids killing of normal healthy cells.

For a given excitation frequency, there exists an optimum nanoparticle size that yields a maximum specific absorption rate (SAR) and thus most efficient heating. This technique thus requires magnetic nanoparticles with a narrow core size distribution, to maximise the efficiency of the therapy and minimise the amount of ferrofluid to be administered. The magnetic nanoparticles of the invention are thus particularly well suited to this application, as the synthesis method enables the size of the nanoparticles to be closely controlled.

In another embodiment, the nanoparticles may be linked to therapeutically active substances such as antibodies or tumour-killing drugs. The magnetic properties of the nanoparticles can also be used to target tumours, by using a magnetic field to guide the nanoparticles to the tumour cells. However, use of magnetic field alone to direct nanoparticles to tumour cells is not always feasible or accurate, so the present invention provides an advantage by enabling the nanoparticles to be specifically directed to tumour cells via tumour-specific ligands. This may enable less drug to be used and reduce the chance of side effects, as the drug is directed only to the cells where it is needed and not to healthy cells.

In a further aspect, the magnetic nanoparticles of the invention may be used to improve the quality of magnetic resonance imaging (MRI). MRI does not always provide enough contrast to enable structures such as tumours to be efficiently viewed, but the images obtained can be enhanced by using magnetic nanoparticles as contrast media. The enhanced sensitivity thus obtained enables tumours to be detected while still very small and permits detection of tumours at a very early stage when there is more chance of successful treatment.

Detection of tumour cells in this way can also be combined with hyperthermia: once the tumour cells are identified, laser or near IR light may de directed to the tumour site to kill the cells.

Moreover, at present, the lungs cannot be imaged by MRI scanning. Positron emission tomography (PET) can image the lungs, but cannot be used for patients requiring regular scans such as asthma and emphysema patients due to the hazards of repeated exposure to radiation. Recent work has shown that hyperpolarised gas MRI can be applied to diseases such as asthma as the magnetisation of these gases is sufficient enough for an image of an entire lung to be taken in the few seconds it takes a patient to inhale, hold their breath and exhale. The capacity to take images as a patient inhales and exhales can also produce dynamic images as the patient breathes in and out using MRI. The magnetised glyconanoparticles, and in particular those containing gadolinium, can be produced as small as 0.8 nm. Particles this small can effectively be considered "a magnetised gas" and therefore may be usable for lung imaging in a far more convenient setting than the use of hyperpolarised gases.

The ligand-bound particles of the present invention can be delivered specifically to tumour cells so even tumour cells which have moved away from the original tumour site may be targeted for therapy.

Embodiments of the present invention which have a core comprising elemental magnetic metal are particularly well suited to imaging applications, as elemental metal is a more efficient enhancer of imaging then metal oxide. The presence of a passive metal in the core is advantageous as it inhibits oxidation of the magnetic metal. The passive metal also increases the biocompatibility of the nanoparticles and permits the core to be bound to ligands, which in addition to their biological uses further protect the magnetic metal from oxidation and reduce the likelihood of agglomeration.

Another advantage of the nanoparticles of the present invention is their exceptionally small size, which makes them more likely to be taken up by cells even when linked to targeting or therapeutic molecules.

In a farther aspect, the magnetic nanoparticles of the invention may be used to replace radioactive materials used as tracers for drug delivery. Use of magnetic particles instead of radioactive materials permits drug delivery to be assessed by measuring magnetic variations, eliminating potential harm from radiation.

In general, it has been a difficult problem in the art to detect or modulate carbohydrate-mediated interactions since the binding of carbohydrates to other species such as proteins or other carbohydrates is very weak and tends to be polyvalent. Thus, for detection the binding is weak and for modulating interaction, monovalent agents have only had a limited success in disrupting polyvalent carbohydrate based interactions.

In embodiments of the invention relating to carbohydrate-carbohydrate interactions, two types of interaction can be identified. In homophilic interactions, identical carbohydrates interact with one another and could be detected by steadily increasing the concentration of particles having a single species of ligands immobilised on their surface until aggregation occurs. This may be detected by light scattering or electronic effects.

Heterophilic interactions can be detected by mixing together two or more different nanoparticles and determining the aggregation state of the particles.

Thus, the present invention provides a versatile platform for studying and modulating carbohydrate-mediated interactions. For example, the particles could be used to detect anti-carbohydrate antibodies, detecting the binding of antibody to the ligands on the particle via light scattering to pick up aggregation of the particles, or electric field effects, such as surface plasmon resonance, which would be modified when the metal atoms in the particles cluster together.

The invention thus provides a method of determining whether a carbohydrate mediated interaction occurs, the method comprising contacting one or more species suspected to interact via a carbohydrate mediated interaction with the nanoparticles of the invention, and determining whether the nanoparticles modulate the carbohydrate mediated interaction.

The invention also provides a method of disrupting an interaction between a carbohydrate and a binding partner, the method comprising contacting the carbohydrate and the binding partner with the nanoparticles of the invention, wherein the nanoparticles comprise a carbohydrate group capable of disrupting the interaction of the carbohydrate and the binding partner.

In a further aspect, nanoparticles in which the ligand is an antigen can be administered as a vaccine, e.g. ballistically, using a delivery gun to accelerate their transdermal passage through the outer layer of the epidermis. The nanoparticles can then be taken up, e.g. by dendritic cells, which mature as they migrate through the lymphatic system, resulting in modulation of the immune response and vaccination against the antigen.

Nanoparticles in which the ligand is nucleic acid encoding an antigen may also be administered as a vaccine. Nanoparticles are particularly well suited to such applications because nucleic acid vaccines must enter individual cells to be effective, so it is important that particles small enough to penetrate the cell membrane without damaging the cells be used.

Vaccine delivery guns known in the art power delivery by use of compressed air or gas, usually helium gas. This can be painful and causes weals on the skin. The magnetic nanoparticles of the invention could be used in an alternative delivery system whereby the power for delivering the particles is provided by application of a magnetic field. Reversal of the magnetic field would result in rapid acceleration of the nanoparticles, sufficient to propel them through the outer epidermal layer. This would reduce pain and weal formation resulting from the use of compressed gas.

In a further application, it is known that cell surface carbohydrates act as ligands for viral or bacterial receptors (called adhesins) and that binding of the carbohydrates to the receptors is an event required during infection. Synthetic carbohydrates, e.g. glycoconjugates, that are capable of modulating these interactions can be immobilised in the nanoparticles of the invention and used as reagents to study these interactions and as therapeutics to prevent viral or bacterial infection.

In a further application, the present invention may be useful in the modulation of immune response, e.g. following transplantation. As the immunological recognition of tissue begins with carbohydrate mediated interactions between surface carbohydrates present on transplanted tissue and the components of the host's immune system such as antibodies, so this can be targeted to ameliorate immune reactions that result from this interaction. By way of example the carbohydrate Galα1-3Galβ1-4GlnAc (the "αGal" epitope) has been implicated as an important antigenic epitope involved in the rejection of transplanted tissue. Thus, modulation of the interaction of the αGal epitope and the immune system may be a therapeutic target for the nanoparticles described herein.

An alternative approach may be useful in the treatment of cancer as many tumour associated antigens or tumour autocrine factors are carbohydrate based. In this event, the nanoparticles could be provided as vaccines to prime the immune system to produce antibodies which are capable of attacking tumour cells presenting the carbohydrates on their surface. In this regard, it is known that many tumour cells possess aberrant glycosylation patterns which may enable the immune response stimulated by nanoparticles to be directed specifically to tumour cells as opposed to normal, healthy cells. The nanoparticles can also be used to inhibit metastatis in cancer, e.g. through the migration of tumour cells through the endothelial cells.

Non-invasive detection of clinically occult lymph-node metastases in prostate cancer has already been demonstrated by using lymphotropic superparamagnetic nanoparticles in conjunction with MRI. Listed below are examples of glyconanoparticles that may have increased affinity or specificity for metastases.

| | | |
|---|---|---|
| Le$^x$-GNP | Le$^y$-GNP | STn-GNP |
| Globo-H-GNP | Gg$^3$-GNP | Gluco-GNP |
| Malto-GNP | Lacto-GNP | Man-GNP |

In addition to other ligands that might be present such as glyconanoparticles, hormones such as oestrogen, DHEA, etc, can also be attached to the nanoparticles and solubilised. These may have use in the detection of cancers such as breast. Peptides can also be attached to nanoparticles that localise to specific receptors such as cell surface oncogene coded receptors. Lipids, in particular those binding to the toll receptors, can also be attached. Chemical ligands such as methylene blue can be attached to the glyconanoparticles that may be of use in the detection of melanoma metastasis. Finally, siRNA nanoparticles can be made which, after uptake into the cell, could image the expression of oncogene or viral-specific mRNA.

In a further aspect, the nanoparticles can be used as carriers to raise antibodies capable of specifically binding the ligand. This is particularly advantageous where the ligand is a carbohydrate, as it can be a challenging problem in the art to raise antibodies against carbohydrates-containing moieties as they are often small and do not cause strong immune responses.

In a further aspect, carbohydrates can be attached to nanocrystals of cadmium selenide to provide quantum dots, which can then be guided to the required cellular structure by nanoparticles. Other anions such as sulphide may be used in addition to selenide. Quantum dots have potential uses in biological imaging, in both electronic and optical devices, quantum computers and the screening of candidate drugs.

In a further aspect, the present invention includes the use of the nanoparticles defined herein for the assessment of myocardial salvage, i.e. the amount of heart tissue remaining viable after a heart attack. At present this is predominantly monitored by scintigraphic techniques (e.g. SPECT)—using compounds such as sestamibi or tetrofosmin, which can be taken up by cells, in conjugation with radionuclides such as technetium. The uptake of the radioactive tracers is proportional to regional blood flow and thus gives an indication of the degree of myocardial salvage—the greater the uptake, the greater the myocardial salvage.

Compounds such as sestamibi or tetrofosmin work because they are lipophilic cationic complexes that passively diffuse across cell membranes. The functionalised ligands of such complexes can easily be incorporated as surface ligands during the self-assembly of magnetised nanoparticles. A wide variety of other novel chemical ligands can be attached to the nanoparticles to make them freely diffusible.

The nanoparticles described herein may be self-assembled in the presence of derivatives of sestamibi, tetrofosmin or other compounds which permit diffusion into cells. The resulting nanoparticles may then be used to allow myocardial salvage to be monitored by magnetic imaging, without the need for radioactivity. Magnetic resonance imaging may be used to detect the nanoparticles; as for radioactive tracers, uptake of nanoparticles will be proportional to regional blood flow. The scintigraphic tracers most commonly used at present are 99mTc-sestamibi and 99m-tetrofosmin (Recent Advances in 99Tc Radiopharmaceuticals—Annals of Nuclear Medicine 16:79-93 (2003); Contributions of Nuclear Cardiology to Diagnosis and Prognosis of Patients with Coronary Artery Disease—Circulation 2000: 101:1465-1478). In a preferred aspect, the nanoparticles of the invention are conjugated to sestamibi and used for magnetic imaging. In this way, nanoparticles may be used to substitute for 99mTc to monitor myocardial salvage.

In a further application, the magnetic nanoparticles disclosed herein may be used in the production of magnetic recording media.

Embodiments of the present invention will now be described by way of example and not limitation with reference to the accompanying figures.

DETAILED DESCRIPTION

Pharmaceutical Compositions

Figure 1:
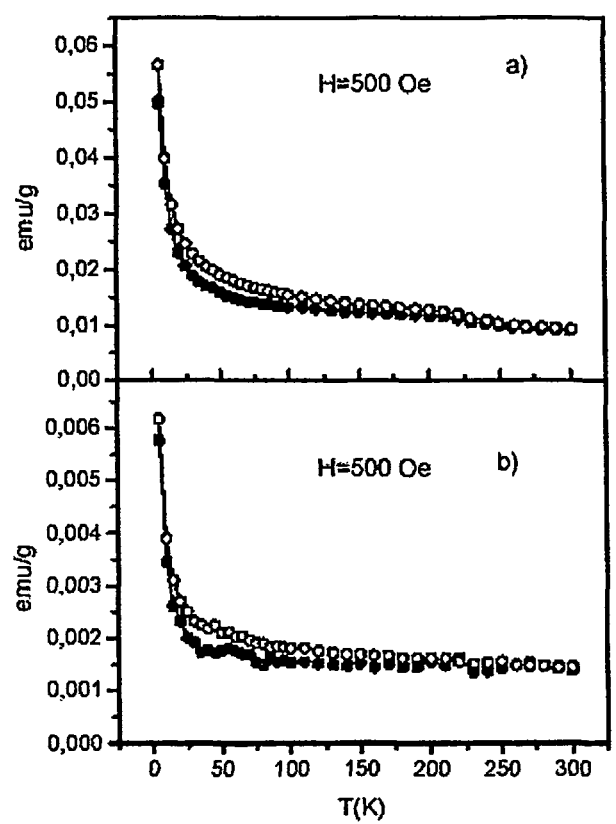
FIG. 1 shows the Zero-Field Cooling (ZFC, bold symbols) and the Field Cooling (FC, empty symbols) curves for lacto-AuFe glyconanoparticles (a) and the malto-AuFe glyconanoparticles (b).

The nanoparticles described herein or their derivatives can be formulated in pharmaceutical compositions, and administered to patients in a variety of forms. Thus, the nanoparticles may be used as a medicament for tumour targeting and hyperthermic therapies, for in vivo cell and tissue labelling, or as contrast enhancement media in magnetic resonance imaging.

Pharmaceutical compositions for oral administration may be in tablet, capsule, powder or liquid form. A tablet may include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicizing agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a "prophylactically effective amount" or a "therapeutically effective amount" (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, Mack Publishing Company, Easton, Pa., 19th Edition, 1995, Handbook of Pharmaceutical Additives, 2nd Edition (eds. M. Ash and I. Ash), 2001 (Synapse Information Resources, Inc., Endicott, N.Y., USA), and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

Antibodies

The nanoparticles may be used as carriers for raising antibody responses against the ligands linked to the core particles. These antibodies can be modified using techniques which are standard in the art. Antibodies similar to those exemplified for the first time here can also be produced using the teaching herein in conjunction with known methods. These methods of producing antibodies include immunising a mammal (e.g. mouse, rat, rabbit, horse, goat, sheep or monkey) with the nanoparticle(s). Antibodies may be obtained from immunised animals using any of a variety of techniques known in the art, and screened, preferably using binding of antibody to antigen of interest. Isolation of antibodies and/or antibody-producing cells from an animal may be accompanied by a step of sacrificing the animal.

As an alternative or supplement to immunising a mammal with a nanoparticle, an antibody specific for the ligand and/or nanoparticle may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the nanoparticles, or may be one constructed using sequences obtained from an organism which has been exposed to the antigen of interest.

The term "monoclonal antibody" refers to an antibody obtained from a substantially homogenous population of antibodies, i.e. the individual antibodies comprising the population are identical apart from possible naturally occurring mutations that may be present in minor amounts. Monoclonal antibodies can be produced by the method first described by Kohler and Milstein, Nature, 256:495, 1975 or may be made by recombinant methods, see Cabilly et al, U.S. Pat. No. 4,816,567, or Mage and Lamoyi in Monoclonal Antibody Production Techniques and Applications, pages 79-97, Marcel Dekker Inc, New York, 1987.

In the hybridoma method, a mouse or other appropriate host animal is immunised with the antigen by subcutaneous, intraperitoneal, or intramuscular routes to elicit lymphocytes that produce or are capable of producing antibodies that will specifically bind to the nanoparticles used for immunisation. Alternatively, lymphocytes may be immunised in vitro. Lymphocytes then are fused with myeloma cells using a suitable fusing agent, such as polyethylene glycol, to form a hybridoma cell, see Goding, Monoclonal Antibodies: Principles and Practice, pp. 59-103 (Academic Press, 1986).

The hybridoma cells thus prepared can be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody producing cells, and are sensitive to a medium such as HAT medium.

Culture medium in which hybridoma cells are growing is assayed for production of monoclonal antibodies directed against the nanoparticles/ligands. Preferably, the binding specificity is determined by enzyme-linked immunoabsorbance assay (ELISA). The monoclonal antibodies of the invention are those that specifically bind to the nanoparticles/ligands.

In a preferred embodiment of the invention, the monoclonal antibody will have an affinity which is greater than micromolar or greater affinity (i.e. an affinity greater than $10^{-6}$ mol) as determined, for example, by Scatchard analysis, see Munson & Pollard, Anal. Biochem., 107:220, 1980.

After hybridoma cells are identified that produce neutralising antibodies of the desired specificity and affinity, the clones can be subcloned by limiting dilution procedures and grown by standard methods. Suitable culture media for this purpose include Dulbecco's Modified Eagle's Medium or RPM1-1640 medium. In addition, the hybridoma cells may be grown in vivo as ascites tumours in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Nucleic acid encoding the monoclonal antibodies of the invention is readily isolated and sequenced using procedures well known in the art, e.g. by using oligonucleotide probes that are capable of binding specifically to genes encoding the heavy and light chains of murine antibodies. The hybridoma cells of the invention are a preferred source of nucleic acid encoding the antibodies or fragments thereof. Once isolated, the nucleic acid is ligated into expression or cloning vectors, which are then transfected into host cells, which can be cultured so that the monoclonal antibodies are produced in the recombinant host cell culture.

Hybridomas capable of producing antibody with desired binding characteristics are within the scope of the present invention, as are host cells containing nucleic acid encoding antibodies (including antibody fragments) and capable of their expression. The invention also provides methods of production of the antibodies including growing a cell capable of producing the antibody under conditions in which the antibody is produced, and preferably secreted.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope, here a carbohydrate ligand as defined herein.

Examples of antibody fragments, capable of binding an antigen or other binding partner, are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and $F(ab')_2$ fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies, humanised antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. Cloning and expression of chimeric antibodies are described in EP 0 120 694 A and EP 0 125 023 A.

EXPERIMENTAL SECTION

Example 1

Au—Fe Nanoparticles

Figure 3:
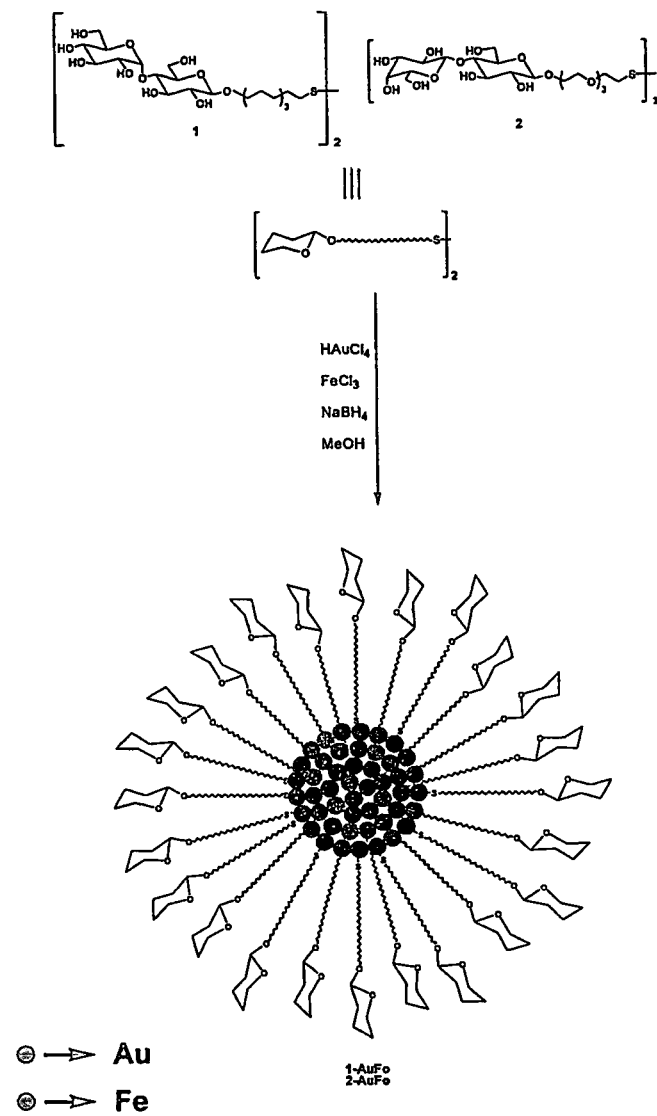
FIG. 3 depicts schematically the synthesis the magnetic glyconanoparticles.
Figure 4A:
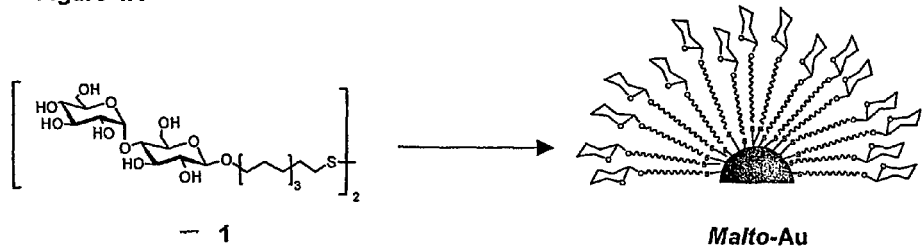
FIG. 4 shows a) The neoglycoconjugate 1 used for the preparation of the malto-Au glyconanoparticles and the corresponding TEM micrograph and histogram; b) the $^1$H-NMR in $D_2O$ and DMSO-$d_6$ of the of the malto-Au nanoparticles.
Figure 4A:
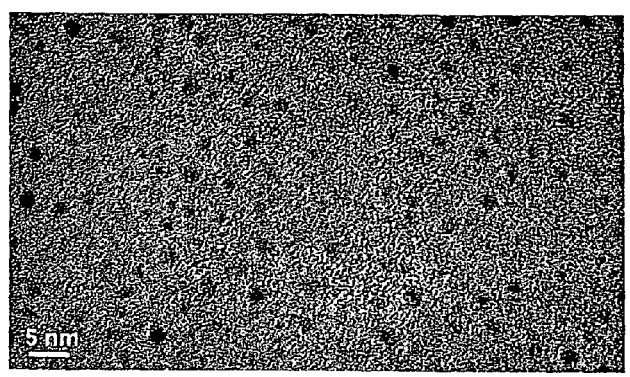
Figure 4A:
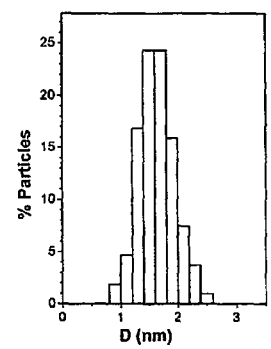
Figure 4B:
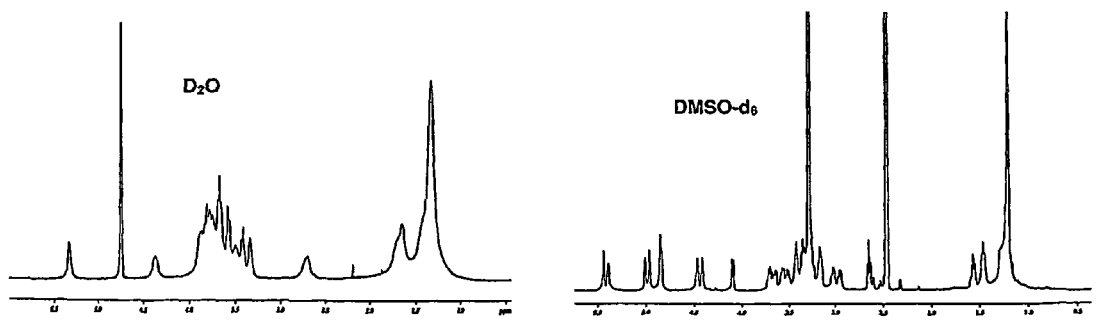

A method of synthesising magnetic glyconanoparticles covalently bound to ligands was devised. By way of example, thiol derivatised neoglycoconjugates 1 and 2 of two significant oligosaccharides, the non-antigenic disaccharide maltose (Glcα(1→4)Glcβ1-OR) and the antigenic lactose (Galβ(1→4)Galβ1-OR), were prepared to functionalise in situ magnetic nanoparticles (FIG. 3, scheme 1). The synthesis of the disulfides 1 and 2 was carried out by glycosidation of the conveniently protected maltose and lactose derivatives with 11-acetylthio-undecanol and 11-acetylthio-3,6,9-trioxa-undecanol, respectively.[12] Both linkers have been used to test the influence of their hydrophobic or hydrophilic nature in the properties of the whole material. Compounds 1 and 2 were isolated as disulfide forms, and used in this form for the preparation of gold-iron protected glyconanoparticles. The water-soluble glyconanoparticles 1-AuFe (malto-AuFe) and 2-AuFe (lacto-AuFe) were obtained in methanol/water mixtures using one-pot synthesis. $FeCl_3$ and $HAuCl_4$ in a ratio 1:4 were reduced with $NaBH_4$ in the presence of disulphides 1 or 2. The protection of the metal core with the neoglycoconjugate monolayers results in highly stable and bio-functional nanoclusters. They have been purified by means of centrifugal filtering and characterised by $^1$H-NMR, UV-vis, ICP, TEM, EDX and SQUID.

Iron analysis of the particle, carried out by means of inductively coupled plasma-atomic emission spectrometry (ICP), indicated 0.27% and 2.81% iron content for 1-AuFe and for 2-AuFe, respectively. These data correspond to an average Au:Fe ratio of 5:0.1 and 5:1 respectively. FIG. 1 shows Zero-Field Cooling and Field Cooling magnetisation curves obtained for the lacto-AuFe (A) and malto-AuFe (B) nanoparticles by means of Superconducting Quantum Interference Device (SQUID) between 5 k and 300 k in a field of 500 Oe. From the magnetic measurements it is inferred that both a superparamagnetic and ferromagnetic behaviour are present between 5 k and 300 k. SQUID measurements confirm the superparamagnetic character of the glyconanoparticles which have a blocking temperature ($T_B$) below 5K (FIG. 1), which would be expected for a magnetic nanoparticle of 2 nm diameter. The superparamagnetic component is clearly observed from a) the partial fitting of the experimental thermal dependence of magnetisation to the Curie-Weiss law; b) the partial dependence of the hysteresis loop on the ration between the applied field and the temperature (H/T); and c) the difference between ZFC and FC curves.

Figure 2A:
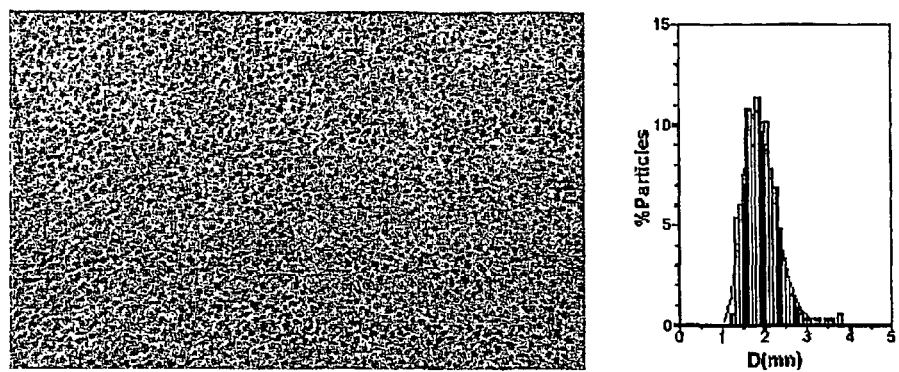
FIG. 2 shows transmission electron micrographs (left) and core size distribution histograms (right) for the lacto-AuFe glyconanoparticles (A) and the malto-AuFe glyconanoparticles (B).

FIG. 2 shown transmission electron micrographs (left) and core-size distribution histograms (right) for the lacto-AuFe (A) and malto-AuFe (B) nanoparticles. Each black dot corresponds to a single particle. The dots are regularly separated by the ligands (neoglycoconjugate) attached to the core and they form ordered monolayers. The TEM was recorded at a 200 kV electron beam energy on a Philips CM200 microscope.

Figure 2B:
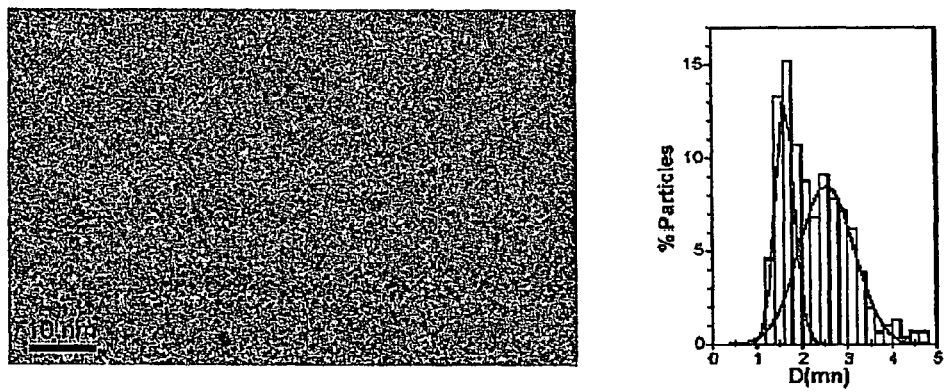

In the case of the 2-AuFe sample (lacto-AuFe), the glyconanoparticles are dispersed, spherical and homogeneous. The mean diameter of the gold/iron cluster was evaluated to be 2 nm. A few isolated particles with a size of about 10 nm have been found in some regions of the grid, but these particles have not been included in the histogram. In the case of the sample 1-AuFe (malto-AuFe) the glyconanoparticle presents a bimodal particle size distribution, as indicated by the corresponding histogram (FIG. 2B). Particles with a mean diameter of the gold/iron cluster about 2.5 nm and less than 1.5 nm have been found. Worthy of note is the spontaneous formation of aligned chains in extended regions of the grid, indicating an additional magnetostatic force (FIG. 2B) This behaviour could be attributed to dipole-dipole magnetic forces or quantum tunnelling among the nanoparticles. The aligned arrangement was not observed in the micrographs obtained for the 2-AuFe nanodots, although a high ordered monolayer is observed.

Preparation $MaltoC_{11}SauFe$:

A solution of $FeCl_3$ (2 mg; 0.013 mmol; 0.25 equiv) in water (0.5 mL) was added to a solution of disulfide 1 (80 mg; 0.075 mmol; 3 equiv.) in MeOH (11.5 mL) followed by the addition of a solution of $HauCl_4$ (17 mg; 0.05 mmol; 1 equiv) in water (2 mL). $NaBH_4$ 1 M (52 mg; 1.38 mmol; 27.5 equiv) was then added in small portions with rapid stirring. The black suspension formed was stirred for an additional 2 h and the solvent removed under vacuum. The glyconanoparticles are insoluble in MeOH but soluble in water.

$LactoEG_4SauFe$:

A solution of $FeCl_3$ (1 mg; 0.0065 mmol; 0.25 equiv) in water (0.25 mL) was added to a solution of disulfide 2 (70 mg; 0.07 mmol; 5.5 equiv.) in MeOH (12 mL) followed by the addition of a solution of $HAuCl_4$ (8 mg; 0.025 mmol; 1 equiv) in water (1 mL). $NaBH_4$ 1 M (26 mg; 0.69 mmol; 27.5 equiv) was then added in small portions with rapid stirring. The black suspension formed was stirred for an additional 2 h and the solvent removed under vacuum. The glyconanoparticles are insoluble in MeOH but soluble in water.

Purification:

Purification was performed by centrifugal filtration. The crude product was dissolved in water (~15 mL) NANOpure and the solution was loaded into a centrifugal filter device (CENTRIPLUS YM30, MICROCON, MWCO=30000), and subjected to centrifugation (3000×g, 40 min). The dark glyconanoparticle residue was washed with MeOH and water and the process repeated several times until the starting material could no longer be detected by thin layer chromatography (TLC). The residue was dissolved in water and centrifuged several times to eliminate insoluble materials. The clear solution was lyophilised and the products obtained were free of salts and starting material (absence of signals from disulfide and $Na^+$ ions in $^1$H and $^{23}$Na NMR spectroscopy).

Characterization:

TEM examination of the samples was carried out at 200 KV (Philips CM200 microscope). A single drop (20 μL) of the aqueous solutions of the Au/Fe glyconanoparticles were placed onto a copper grid coated with a carbon film. The grid was left to dry in air for several hours at room temperature. Particle size distributions of the Au/Fe clusters were evaluated from several micrographs using an automatic image analyser. EDX analysis was performed with a Philips DX4 equipment attached to the microscope. ICP analysis was performed by Agriquem S. L. following PEC-009 protocol. UV spectra were obtained by a UV/vis Perkin Elmer Lambda 12 spectrophotometer. $^1$H-NMR spectra were acquired on Bruker DRX-500 spectrometers and chemical shifts are given in ppm (δ) relative to $D_2O$.

1-AuFe:

TEM: average diameter of metallic core, 1.5 and 2.5 nm.
ICP: 0.27% Fe
UV ($H_2O$): λ=500 nm, surface plasmon resonance
$^1$H-NMR (500 MHz, $D_2O$) δ: 5.32 (s, 1H, H-1'), 4.37 (s, 1H, H-1), 4.00-3.30 (m, 13H), 2.70 (s, 2H, $CH_2S$), 1.85-1.20 (m, 17H)

2-AuFe:

TEM: average diameter of metallic core, 2 nm.
ICP: 2.81% Fe
UV ($H_2O$): λ=500 nm, surface plasmon resonance
$^1$H-NMR (500 MHz, $D_2O$) δ: 4.49 (brd, 1H, H-1'), 4.40 (brs, 1H, H-1), 4.10-3.30 (m, 23H), 2.92 (m, 0.5H).

Example 2

Magnetic Au Nanoparticles

Water soluble gold glyconanoparticles (GNPs) stabilized with self-assembled monolayers (SAMs) of different carbohydrate molecules were prepared by the chemical reduction of a metal salt precursor in aqueous solution in the presence of an excess of thiol derivatised neoglycoconjugates. The preparation sample procedure used as a starting point the Penadés et al [11][19] that produces gold GNPs in which the metal cluster has been at same time protected and functionalised with the organic molecule. The formation of Au—S covalent bonds isolate the metal cluster preventing its growth (core diameter≈2 nm) and confer on the nanoclusters exceptional stability in solution.

In this example, we report on the experimental observation of magnetic hysteresis up to room temperature in gold glyconanoparticles with average diameters of 1.4 and 1.5 nm. By increasing the ratio of thiol:gold in the Penadés procedure, GNPs sample with diameter of less than 1.5 nm can be obtained. This is illustrated by the preparation and the magnetic properties of Au-GNPs obtained using the maltose neoglycoconjugate 1 as thiol linker species (FIG. 4).

Preparation of Gold Glyconanoparticles malto-Au:

An aqueous solution of tetrachloroauric acid (HAuCl4, 0.018 mmol) and an excess of disulfide neoglycoconjugate 1 (0.2 mmol) was reduced with sodium borohydride (NaBH4, 22 equiv) at room temperature. A brown suspension was immediately formed. The suspension was shaken for about two hours, then the solvent was removed and the glyconanoparticles (GNPs) were purified by washing with water and centrifugal filtering (CENTRIPLUS, Mr 30000, 1 h, 3000× g). The residue in the filter was dissolved in water and lyophilized. The GNPs were characterised by transmission electron microscopy (TEM), and $^1$HNMR and UV-visible spectroscopy, induced coupling plasma (ICP) and elemental analysis. TEM: average diameter and; number of Au atoms, 1.5 nm and 79, respectively. UV-VIS ($H_2O$): $\lambda$=520 nm. ICP: 28% Au. Elemental analysis calculated for $(C_{23}H_{43}O_{11}S)_n$ $Au_n$ (n=79): C, 38.18; H, 5.98; S, 4.40; Au, 27.18. Found: C, 39.5; H, 6.07; Au, 28.0.

Figure 5:
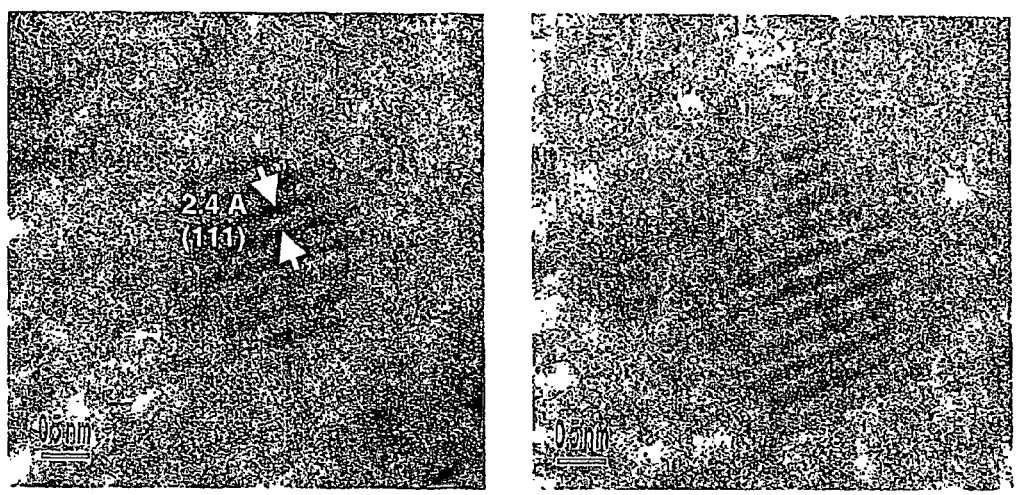
FIG. 5 shows HRTEM of malto-Au glyconanoparticles showing the fcc structure.

FIG. 4 shows in a) the synthetic scheme for the malto-Au GNPs and the corresponding TEM micrographs for the malto-Au GNPs and the corresponding particle size distribution histograms for the samples; and in b) the $^1$HNMR spectra in $D_2O$ and in DMSO-$d_6$ are also shown. The malto-Au GNPs present, in all the cases, narrow particle size distribution with an average size of 1.5 nm or less. High resolution electron micrograph (HRTEM) indicating the fcc structure of the thiol protected malto-Au GNPs is show in FIG. 5.

Superconducting Quantum Interference Devise (SQUID) magnetometry indicated ferromagnetic behaviour even up to room temperature. Hysteresis loop measured at 5K exhibits a coercive field of 120 Oe. The blocking temperature, obtained from the thermal dependence of coercivity, was found to be 395 K that corresponds to an effective anisotropy constant of 10 meV/atom which is similar to that observed in a single Co atom onto platinum (III) surface [20]. The magnetisation did not conform to the Curie-Weiss law, but showed a much slower T-dependence. An atomic magnetic moment of around 0.003 PB per Au atom was derived from low T magnetic measurements.

Figure 6:
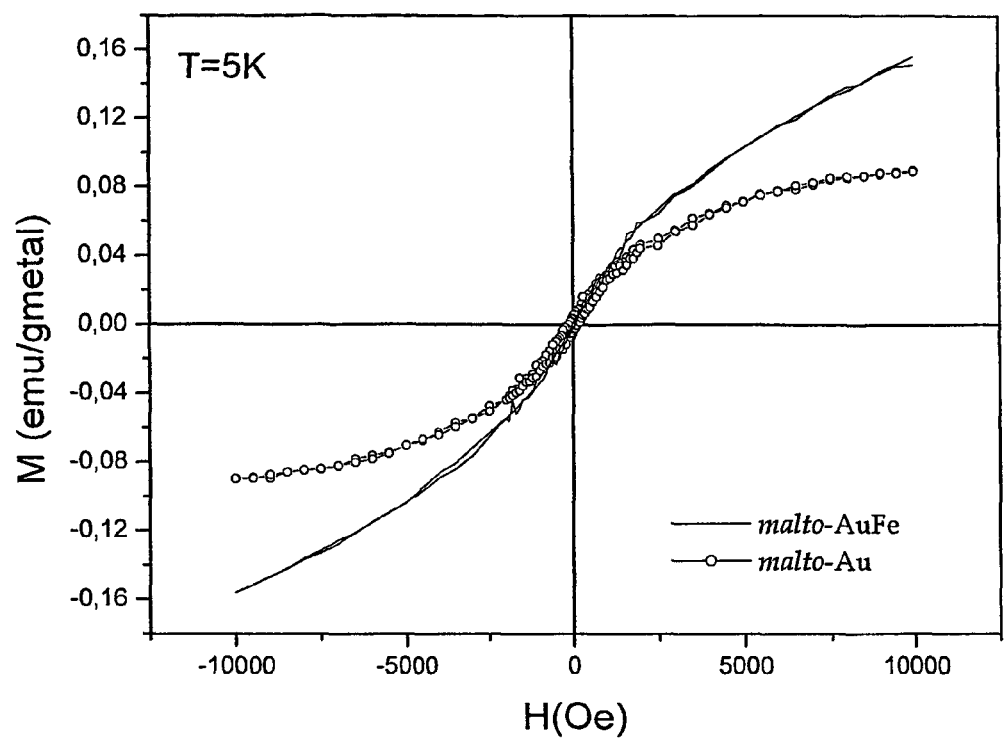
FIG. 6 shows hysteresis loops corresponding to 1.5 nm gold-thiol protected of malto-Au glyconanoparticles at 5 K. The magnetization is given in emu per gram of gold, i.e, no contribution of the magnetization coming from ligand is assumed.

FIG. 6 show the hysteresis loops measured at 5K for gold thiol capped malto-Au GNPs. It is evident from FIG. 5 the magnetization process of thiol protected glyconanoparticles exhibit similar behaviour as typical ferromagnetic materials describing a hysteresis loops even at room temperature. In addition, it was observed that the samples are not saturated at any temperature. Remanence values around half of the magnetisation value at 1 T are measured, which implies that atoms as well as GNPs hold a permanent magnetic moment and that the gold GNPs system consists of an assembly of magnetic moments randomly distributed in orientation.

One can argue whether the observed behaviour is due to the presence of ferromagnetic impurities. Inductive Coupled Plasma (ICP) analysis indicated that the amount of Fe impurities (0.007% wt.) in the malto-Au is very low to account for the obtained magnetization values. In spite of that analysis, samples of malto-Au Fe GNPs containing 0.2% wt of iron have been prepared to characterized the influence of Fe on the magnetic behavior. FIG. 6 shows the hysteresis loops measured at 5 K for both set of GNPs. It is clear that the presence of increased amounts of iron (ferromagnetic impurities) in the malto-AuFe nanoparticles reduces the ferromagnetic behaviour at this temperature, whereas the hysteresis loop still remains for malto-Au samples. As the GNPs are dispersed, inter-particle interactions can only be of magnetostatic nature. The average distance between gold core is determined by the length of two consecutive molecules of the maltose neoglycoconjugate 1 (6 nm). As the permanent magnetic moment of each particle is very low, the magnetic field acting on a GNP by a single neighbour GNP is lower than 10 Oe. Therefore, the influence of the stray fields can be neglected.

Since bulk Au is diamagnetic, the ferromagnetic behaviour may be due to the combination of both size and bonding effects [21]. The discrete electronic energy structure [22], the presence of stacking faults [23], as well as the extremely high percentage (≥80%) of surface atoms [24], covalently bonded to S, may be the possible causes of the onset of ferromagnetism.

In conclusion, it has been shown (FIG. 6) that very small thiol protected gold glyconanoparticles exhibit a localized permanent magnetism in contrast to the metallic diamagnetism characteristic of other non-thiol protected gold nanoparticles or bulk gold. This observation point out that the thiol-gold bonding induces in gold glyconanoparticles permanent magnetic moments probably associated with the extra d-holes localized near to the Au bonds. This suggest the technological application of the nanoparticles of the present invention for magnetic recording. Furthermore, the water solubility and the biological label of these GNPs amplify enormously their application in the biological field.

Example 3

Au—Gd (III) Nanoparticles

Gold glyconanoparticle (GNPs) may be complexed to Gd(III) and other lanthanides to give new contrast agent. The neoglycoconjugate ligands present in the GNPs (60 to 100 molecules) are the chelating moiety.

Preparation of lactoEG$_4$-Au(Gd) glyconanoparticles:

To a solution of the corresponding gold glyconanoparticle (20.0 mg) in water (1 mL) a solution of $GdCl_3$.(0.5 M, 1.08 mL) was added. The mixture was stirred in the absence of light during 20 h. The solution was filtered by centrifugation (MICROCON YM30, 13000 rpm, 8 min). The residue was washed (8×0.5 mL, methanol/water, ⅓). The nanoparticles were dissolved in water and lyophilized to give 17.5 mg of dark violet nanoparticles. TEM: average diameter 2.5 nm. EDX: Gd 6.8%; Au 33.2% atomic.

Figure 7A:
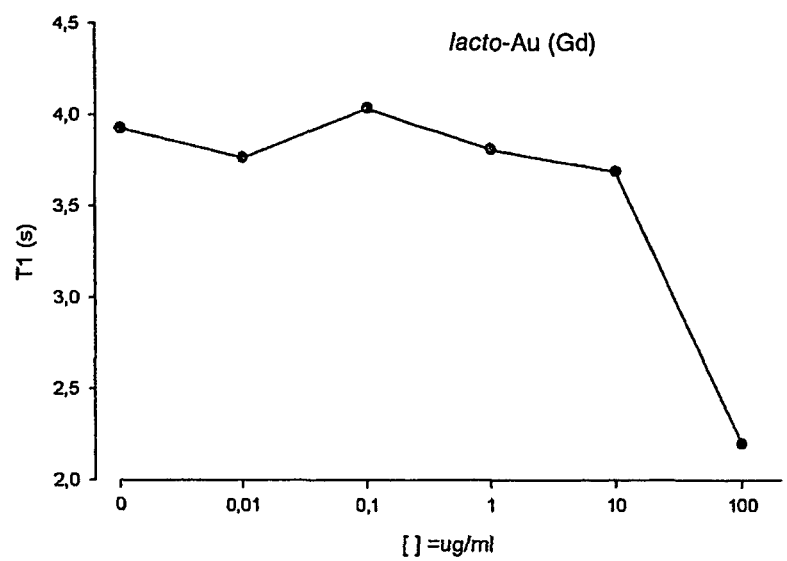
FIG. 7 show changes in the $T_1$ (A) and $T_2$ (B) values of of malto-Au glyconanoparticles with increasing Gd (III) concentration.
Figure 7B:
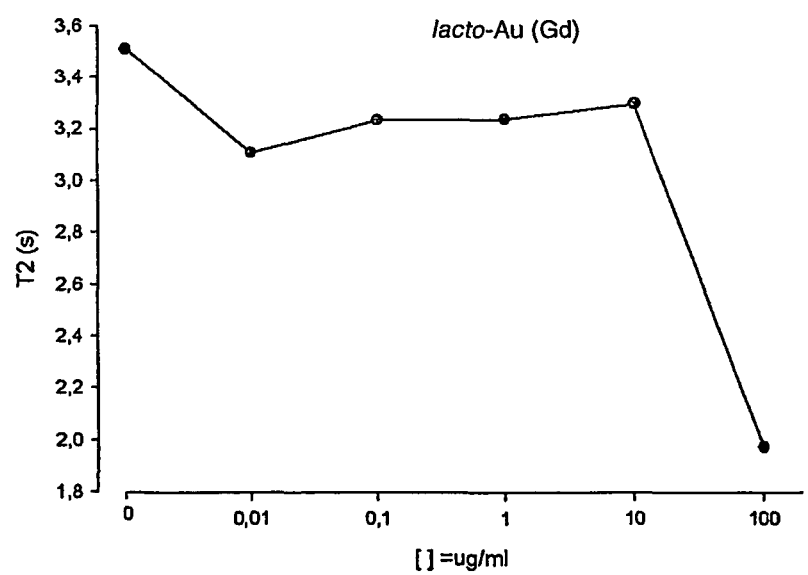
Figure 8A:
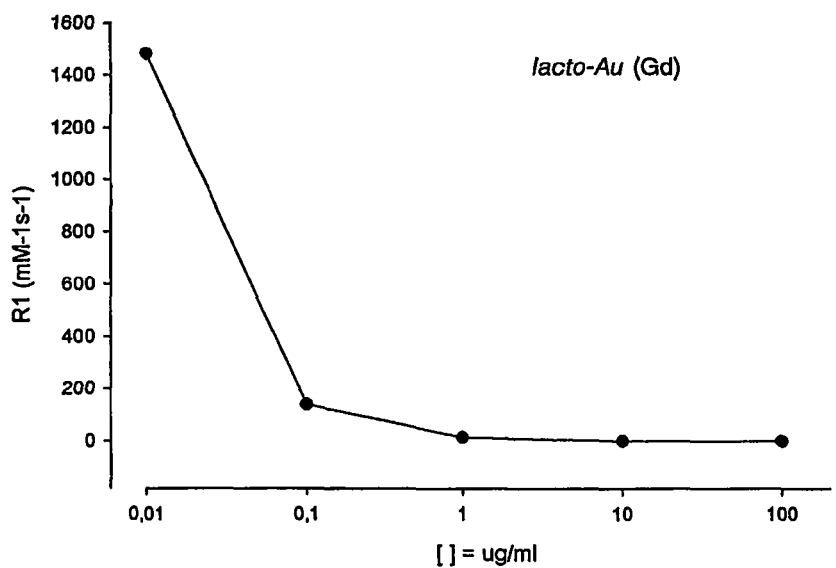
FIG. 8 show changes in the $r_1$ (A) and $r_2$ (B) values of malto-Au glyconanoparticles with increasing Gd(III) concentration.
Figure 8B:
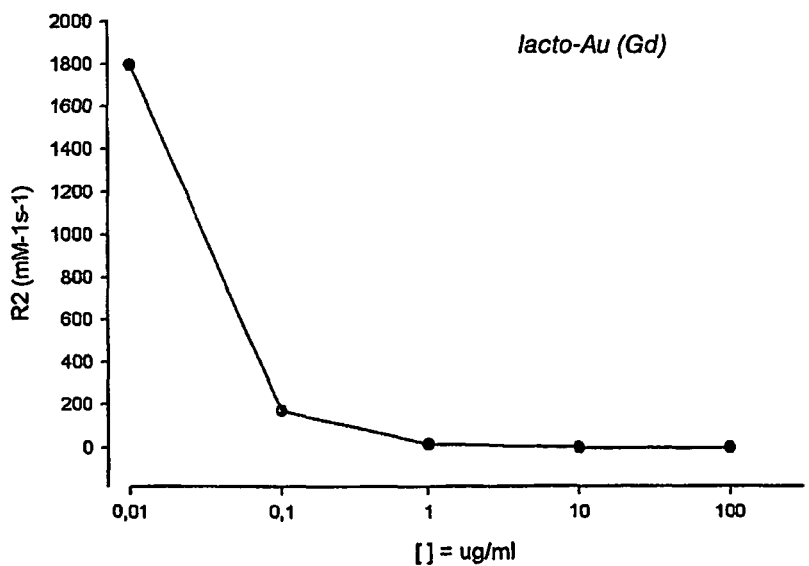

Determination of Relaxivities:

$^1$H NMR relaxation times $T_1$ and $T_2$ (37° C., pH 7.2) of the water protons in aqueous solution were measured at 1.5 Tesla in a Brucker Minispec NMR spectrometer. $T_1$ values were determined by the inversion-recovery method and the $T_2$ values were determined by the Carr-Purcell-Maiboom-Gill sequence. Solutions of the lacto-Au(Gd) nanoparticles at five different concentration (0.01, 0.1, 1, 10, 100 μg/mL) were prepared in Hepes buffer with 150 mM of NaCl. The relaxivities were calculated from the differences in longitudinal and transversal relaxation rates ($1/T_{1(2)}$) of the water protons in the presence and absence of the glyconanoparticles, and the concentration of Gd(III) expressed in mM. FIGS. 7 and 8 show the results.

In conclusion, in the examples shown herein, the inventors have developed a simple methodology to prepare water-soluble, superparamagnetic nanoparticles covalently linked to antigenic oligosaccharides. The methodology can be extended to the preparation of hybrid nanoparticles incorporating carbohydrates and other molecules. Carbohydrate-receptor interactions can direct the magnetic glyconanoparticles to target cells and tissues allowing their selective labelling. This demonstrates that this type of polyvalent magnetic glyconanoparticles complements the scarcely available bioactive magnetic nanoparticles.[9][10][17] Accordingly, the easy preparation and purification, their small core size and their stability and solubility in physiologically conditions of nanoparticles of the present invention convert these tools in potential candidates for diagnostic, tumour targeting [15], hyperthermia [16], and magnetic resonance imaging [17] applications.

REFERENCES

The references mentioned herein are all expressly incorporated by reference.

[1] Niemeyer, C. M. *Angew. Chem. Int. Ed.* 2001, 40, 4128-4158.
[2] Bergemann, C.; Müller-Schulte, D.; Oster, J.; Brassard, L.; Lübbe, A. S. *J. Magn. Magn. Mater.* 1999, 194, 45.
[3] Whitesides, G. M.; Kazlauskas R. J.; Josephson L. *Trends Biotechnol.* 1983, 1, 144-148.
[4] Sun, S.; Murray, C. B.; Weller, D.; Folks, L.; Moser, A. *Science* 2000, 287, 1989.
[5] a) Shafi, K. V. P. M.; Gedanken, A.; Prozorov, R. *Adv. Mater.* 1998, 10, 590-593. b) Fried, T.; Shemer, G.; Markovich, G. *Adv. Mater.* 2001, 13, 1158-1161. c) Moumen, N.; Veillet, P.; Pileni, M. P. *J. Magn. Magn. Mater.* 1995, 149, 67-71.
[6] Park, S.-J.; Kim, S.; Lee, S.; Khim, Z. G.; Char, K.; Hyeon, T. *J. Am. Chem. Soc.* 2000, 122, 8581-8282.
[7] a) Suslick, K. S.; Fang, M.; Hyeon, T. *J. Am. Chem. Soc.* 1996, 118, 11960-11961. b) Sun, S.; Zeng H. *J. Am. Chem. Soc* 2002, 124, 8204-8205. c) Guo, Q.; Teng, X.; Rahman, S.; Yang, H. *J. Am. Chem. Soc.* 2003, 125, 630-631.
[8] Sun, S.; Anders, S.; Hamann H. F.; Thiele, J.-U.; Baglin, J. E. E.; Thomson, T.; Fullerton, E. E.; Murray, C. B.; Terris, B. D. *J. Am. Chem. Soc.* 2002, 124, 2884-2885.
[9] a) Josephson, L.; Tung, C.-H.; Moore, A.; Weissleder, R. *Bioconjugate Chem.* 1999, 10, 186-191. b) Lewin, M.; Carlesso, N.; Tung, C.-H.; Tang, X.-W; Cory, D.; Scadden, D. T.; Weissleder, R. *Nat. Biotechnol.* 2000, 18, 410-414.
[10] Josephson, L.; Pérez, J. M.; Weissleder, R. *Angew. Chem. Int. Ed.* 2001, 40, 3204-3206.
[11] de la Fuente, J. M.; Barrientos, A. G.; Rojas, T. C.; Rojo, J.; Cañada, J.; Fernández, A.; Penadés, S. *Angew. Chem. Int. Ed.* 2001, 40, 2257-2261.
[12] Barrientos, A. G.; de la Fuente, J. M.; Rojas, T. C.; Fernández, A.; Penadés, S. *Chem. Eur. J.* 2002, 9, 1909-2001.
[13] Hernáiz, M. J.; de la Fuente, J. M.; Barrientos, A. G.; Penadés, S. *Angew. Chem. Int. Ed.* 2002, 41, 1554-1557.
[14] Zhou, W. L.; Carpenter, E. E.; Lin, J.; Kumbhar, A.; Sims, J.; O'Connor, C. J. *Eur. Phys. J. D.* 2001, 16, 289-292.
[15] Mykhaylyk O.; Cherchenko A.; Ilkin A.; Dudchenko N.; Ruditsa V.; Novoseletz M.; Zozulya Y. *J. Magn. Magn. Mater.* 2001, 225, 241-247.
[16] Jordan, A.; Scholz, R.; Wust, P.; Fähling, H.; Felix, R. *J. Magn. Magn. Mater.* 1999, 201, 413-419.
[17] Josephson, L.; Kircher M. F.; Mahmood, U.; Tang, Y.; Weissleder R. *Bioconjugate Chem.* 2002, 13, 554-560.
[18] Taton et al, *Science* 2000 289:1757-1760.
[19] Barrientos A. G. et al., *Chem. Eur. J.* 9, 2003, 1909-1921.
[20] Gambardela, P. et al, Giant Magnetic Anisotropy of Single Cobalt Atoms and Nanoparticles, *Science,* 2003, 300, 1130-1133.
[21] Di Felice, R., Selloni, A., Molinari, E., *J. Phys. Chem. B.,* 2003, 107, 1151-1156.
[22] D. Davidovic and M. Tinkham, *Phys. Rev. Lett.,* 1999, 83 (8), 1644-1647.
[23] Vitos, L., Johansson, B., *Phys. Rev. B.,* 2000, 62 (18), R11957.
[24] Villás, I. M. L., Chàtelain, A., de Heer, W. A., *Science,* 1994, 265, 1682-1684.

The invention claimed is:

1. A method for performing magnetic resonance imaging (MRI) of a site in a patient, said method comprising administering to said patient a MRI contrast agent comprising magnetic nanoparticles, said nanoparticles having a core of metal atoms, wherein the core is covalently linked to a plurality of ligands and has a diameter of less than 2.5 nm, and wherein said metal atoms comprise metal atoms having an oxidation state of zero.

2. The method of claim 1, wherein the imaged site comprises the lungs of said patient.

3. The method of claim 1, wherein the core comprises metal atoms selected from: gold, platinum, silver and copper.

* * * * *

UNITED STATES PATENT AND TRADEMARK OFFICE
CERTIFICATE OF CORRECTION

PATENT NO. : 8,557,607 B2
APPLICATION NO. : 10/559957
DATED : October 15, 2013
INVENTOR(S) : Penades et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1478 days.

Signed and Sealed this

Fifteenth Day of September, 2015

Michelle K. Lee
*Director of the United States Patent and Trademark Office*